United States Patent
Farazi et al.

(10) Patent No.: US 8,135,464 B1
(45) Date of Patent: Mar. 13, 2012

(54) PAINLESS VENTRICULAR RATE CONTROL DURING SUPRAVENTRICULAR TACHYCARDIA

(75) Inventors: Taraneh Ghaffari Farazi, San Jose, CA (US); Gene A. Bornzin, Simi Valley, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 681 days.

(21) Appl. No.: 11/830,499

(22) Filed: Jul. 30, 2007

(51) Int. Cl.
*A61N 1/362* (2006.01)

(52) U.S. Cl. .......................................... 607/9

(58) Field of Classification Search ............ 607/1–10, 607/14, 113–122; 128/697, 419
See application file for complete search history.

(56) References Cited

U.S. PATENT DOCUMENTS

| | | | |
|---|---|---|---|
| 5,074,308 A * | 12/1991 | Sholder et al. ............... | 600/510 |
| 5,203,326 A | 4/1993 | Collins | |
| 5,243,980 A | 9/1993 | Mehra | |
| 5,334,221 A | 8/1994 | Bardy | |
| 5,356,425 A * | 10/1994 | Bardy et al. ................. | 607/14 |
| 5,658,318 A | 8/1997 | Stroetmann et al. | |
| 5,916,239 A | 6/1999 | Geddes et al. | |
| 6,266,564 B1 | 7/2001 | Hill et al. | |
| 6,292,695 B1 * | 9/2001 | Webster et al. ............... | 607/14 |
| 6,922,585 B2 | 7/2005 | Zhou et al. | |
| 6,934,583 B2 | 8/2005 | Weinberg et al. | |
| 7,228,173 B2 * | 6/2007 | Cazares ........................ | 607/14 |
| 7,555,341 B2 * | 6/2009 | Moffitt et al. ................ | 607/14 |
| 7,725,184 B2 * | 5/2010 | Cazares ........................ | 607/14 |
| 2003/0074029 A1 * | 4/2003 | Deno et al. .................... | 607/23 |
| 2003/0078623 A1 | 4/2003 | Weinberg et al. | |
| 2003/0191403 A1 | 10/2003 | Zhou et al. | |
| 2004/0199210 A1 | 10/2004 | Shelchuk | |
| 2005/0187586 A1 | 8/2005 | David et al. | |
| 2005/0261741 A1 | 11/2005 | Libbus et al. | |
| 2007/0250124 A1 * | 10/2007 | Burnes et al. ................ | 607/9 |
| 2008/0091240 A1 * | 4/2008 | Ben-David et al. .......... | 607/4 |

FOREIGN PATENT DOCUMENTS

| | | |
|---|---|---|
| EP | 0547734 A2 | 6/1993 |
| EP | 0547734 A3 | 6/1993 |
| EP | 0547734 B1 | 6/1993 |
| EP | 0721786 A2 | 8/1996 |
| EP | 0721786 A3 | 8/1996 |
| EP | 0721786 B1 | 8/1996 |

OTHER PUBLICATIONS

"Ventricular refractory period extension caused by defibrillation shocks", RJ Sweeney et al, Circulation 1990:82;965-972.*

* cited by examiner

*Primary Examiner* — Carl H Layno
*Assistant Examiner* — Paula J Stice
(74) *Attorney, Agent, or Firm* — Steven M. Mitchell

(57) ABSTRACT

In various embodiments of the present invention, lower amplitude high frequency burst stimulation of cardiac fat pad(s) innervating the AV node and/or ventricle tissue performed in conjunction with ventricular pacing during refractory period is used to reduce the ventricular rate in order to terminate arrhythmias such as supraventricular tachycardia. In an embodiment of the present invention, one or more pace pulse delivered during a ventricular refractory period can be used to further extend the duration of the refractory period followed by a short burst of cardiac fat pad stimulation to temporarily slow AV conduction. In an embodiment of the present invention, this therapy slows the ventricular rate by altering conduction speed in both the AV node and the ventricles.

21 Claims, 6 Drawing Sheets

PAINLESS VENTRICULAR RATE CONTROL DURING SUPRAVENTRICULAR TACHYCARDIA

FIELD OF THE INVENTION

The present invention relates generally to programmable implantable pacemakers, and implantable cardioverter-defibrillators with pacemaker functions, and particularly those devices that perform ventricular pacing.

BACKGROUND

The heart is a pump which pumps blood throughout the body. It consists of four chambers, including a left atrium, a right atrium, a left ventricle and a right ventricle. In order for the heart to efficiently perform its function as a pump, the atrial muscles and ventricular muscles should contract in a proper sequence and in a timed relationship.

In a given cardiac cycle (corresponding to one 'beat' of the heart), the two atria contract, forcing the blood therein into the ventricles. A short time later, the two ventricles contract, forcing the blood therein to the lungs (from the right ventricle) or through the body (from the left ventricle). Meanwhile, blood from the body fills the right atrium and blood from the lungs fills the left atrium, waiting for the next cycle to begin. A typical healthy adult heart can beat at a rate of 60-70 beats per minute (bpm) while at rest, and can increase its rate to 140-180 bpm when the adult is engaging in strenuous physical exercise, or undergoing other physiologic stress.

The healthy heart controls its rhythm from its sino-atrial (SA) node, located in the upper portion of the right atrium. The SA node generates an electrical impulse at a rate commonly referred to as the 'sinus' rate. This impulse is delivered to the atrial tissue when the atria are to contract and, after a suitable delay, propagates to the ventricular tissue when the ventricles are to contract.

When the atria contract, a detectable electrical signal referred to as a P-wave is generated. When the ventricles contract, a detectable electrical signal referred to as the QRS complex (also referred to simply as an 'R-wave') is generated, as a result of the depolarization of the ventricles. The R-wave is much larger than the P-wave, principally because the ventricular muscle tissue is much more massive than the atrial muscle tissue. The atrial muscle tissue need only produce a contraction sufficient to move the blood a very short distance, from the respective atrium to its corresponding ventricle. In contrast, the ventricular muscle tissue must produce a contraction sufficient to push the blood over a longer distance (e.g., through the complete circulatory system of the entire body).

It is the function of a pacemaker to provide electrical stimulation pulses to the appropriate chamber(s) of the heart (atria and/or ventricles) in the event the heart is unable to beat on its own (e.g., in the event either the SA node fails to generate its own natural stimulation pulses at an appropriate sinus rate, or in the event such natural stimulation pulses do not effectively propagate to the appropriate cardiac tissue). Most modern pacemakers accomplish this function by operating in a 'demand' mode where stimulation pulses from the pacemaker are provided to the heart only when it is not beating on its own, as sensed by monitoring the appropriate chamber of the heart for the occurrence of a P-wave or an R-wave. If a P-wave or an R-wave is not sensed within a prescribed period of time (which period of time is often referred to as the 'escape interval'), then a stimulation pulse is generated at the conclusion of this prescribed period of time and delivered to the appropriate heart chamber via a pacemaker lead.

Modern programmable pacemakers are generally of two types: (1) single chamber pacemakers, and (2) dual-chamber pacemakers. In a single chamber pacemaker, the pacemaker provides stimulation pulses to, and senses cardiac activity within, a single-chamber of the heart (e.g., either the right ventricle or the right atrium). In a dual-chamber pacemaker, the pacemaker provides stimulation pulses to, and senses cardiac activity within, two chambers of the heart (e.g., both the right atrium and the right ventricle). The left atrium and left ventricle can also be paced, provided that suitable electrical contacts are made therewith.

A supraventricular tachycardia (SVT) is an arrhythmia that originates in the atria and includes atrial fibrillation (AF) and atrial flutter. Neurostimulation of atrial fat pads and/or parasympathetic neural inputs to atrial fat pads has been shown to modulate: the SA rate, atrioventricular (AV) conduction, the atrial effective refractory period (AERP), and its homogeneity across both atria. In particular, tonic neural activity of the atrial fat pads leads to shortening of the AERP and increases the heterogeneity of refractoriness throughout the atria. Neurostimulation to the coronary sinus region adjacent to the AV nodal fat pad can be used to achieve AV nodal block using high frequency, narrow pulses. However the stimulation levels required to achieve AV block are typically so high that patients report pain. Lower levels of stimulation that are not perceived as painful generally don't produce enough AV slowing to be considered an effective therapy for treating atrial fibrillation (AF). Accordingly, an electric shock is often used to treat AF. However, such treatment is typically painful and drains the battery of the implanted device. Thus, it would be beneficial if non-painful lower energy techniques for terminating AF and other SVT were available.

SUMMARY

Embodiments of the present invention are directed to systems and methods for reducing ventricular rate during a supra ventricular tachycardia (SVT), such as AF. In accordance with an embodiment, an implantable system monitors for a SVT. In response to detecting a SVT, a pacing pulse is delivered to a ventricle during a refractory period following a ventricular activation, to thereby extend the refractory period. Additionally, prior to the next ventricular activation, a burst of stimulation is delivered to one or more cardiac fat pad that innervates atrioventricular (AV) node tissue and/or ventricular tissue, to thereby slow AV node conduction. This scheme can be repeated a plurality of times, e.g. for each of a plurality of consecutive ventricular activations. In specific embodiments, this scheme is repeated until a desired ventricular rate is obtained.

In specific embodiments, the pacing pulse that is delivered during the refractory period is delivered to a ventricle prior to ventricular repolarization. In specific embodiments, the pacing pulse is delivered T1 seconds after the ventricular activation is detected, wherein T1 is between approximately 10 msec-100 msec.

In specific embodiments, the burst of stimulation is delivered approximately 10-30 msec following the pacing pulse. In other embodiments, commencement of the burst of stimulation coincides approximately in time with delivery of the pacing pulse.

In specific embodiments, the duration of the burst of stimulation is T2 seconds, wherein T2 is between approximately 100 msec-1 sec. In specific embodiments, the frequency of the burst of stimulation is between approximately 15 Hz-50

Hz, and pulses of the burst of stimulation have a pulse width between approximately 0.5 msec-3 msec.

In specific embodiments, the amplitude of the burst of stimulation is between approximately 1 volt-10 volts, and preferably does not cause pain to the patient. More specifically, the amplitude at which the patient feels pain in response to the type the burst of stimulation can be determined, e.g., at implant. Then, the implantable device can be programmed such that the amplitude of the bursts of stimulation is less than the amplitude at which the patient feels pain.

This summary is not intended to be a complete description of, or limit the scope of, the invention. Alternative and additional features, aspects, and objects of the invention can be obtained from a review of the specification, the figures, and the claims.

DETAILED DESCRIPTION

Exemplary ICD

Figure 1A:
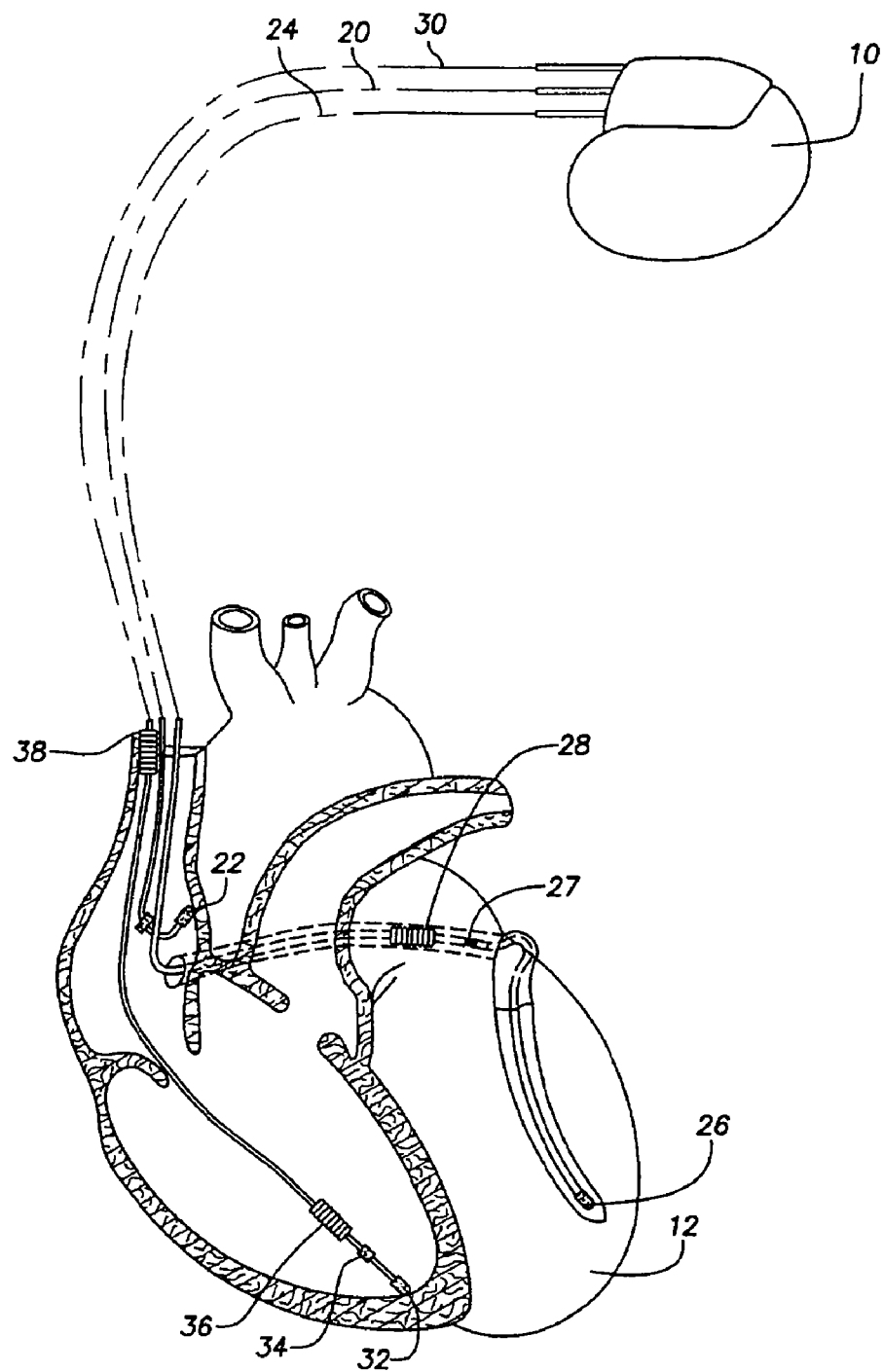
FIG. 1A illustrates an exemplary multi-chamber implantable stimulation device in electrical communication with a patient's heart by way of three or more leads, which are suitable for delivering ventricle pacing and neural tissue stimulation.
Figure 2:
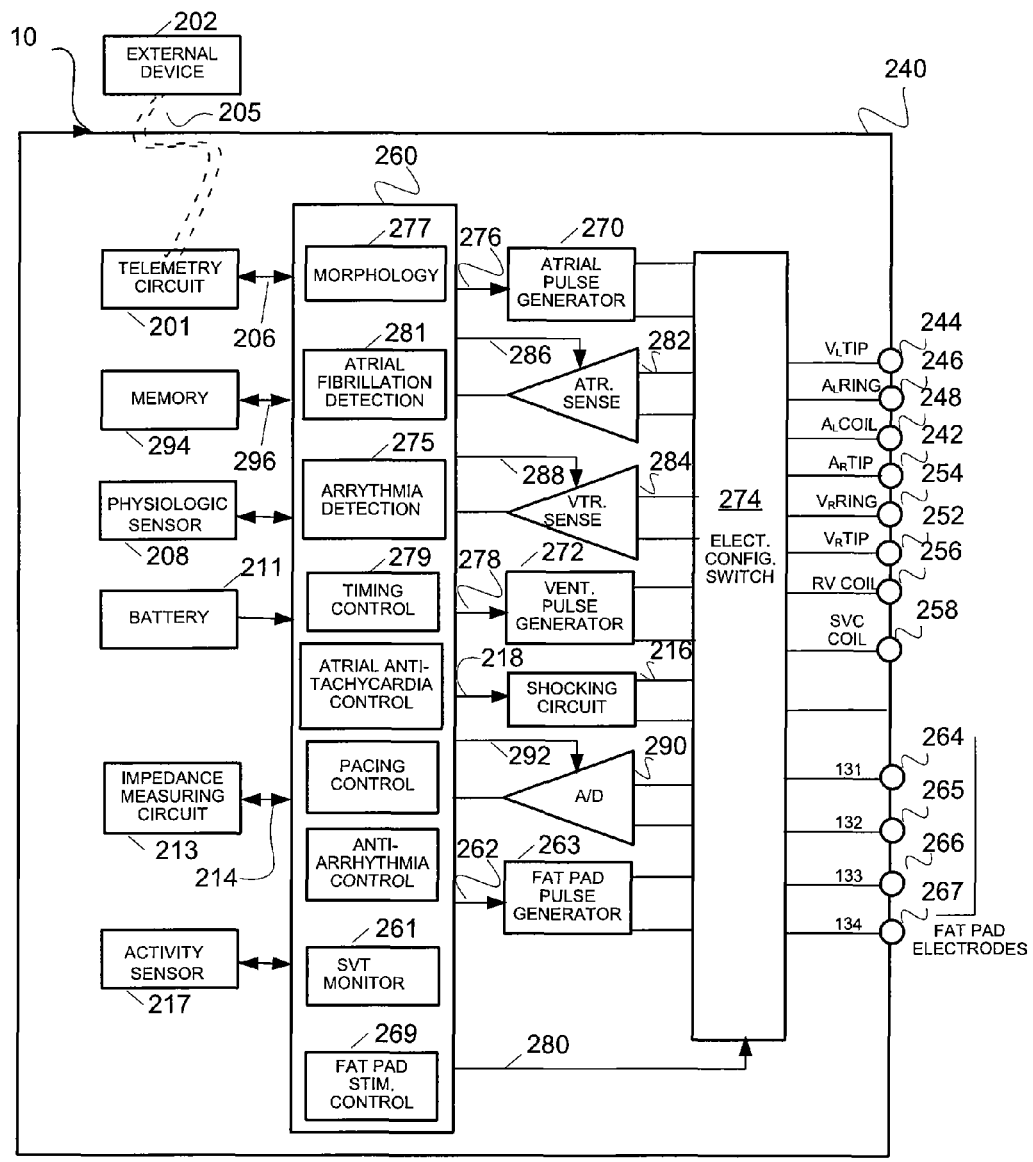
FIG. 2 is a simplified block diagram of the multi-chamber implantable stimulation device of FIG. 1A.

Before describing the invention in detail, it is helpful to describe an example environment in which the invention may be implemented. The present invention is particularly useful in the environment of an implantable cardiac device that can monitor electrical activity of a heart and deliver appropriate electrical therapy, including, ventricular pacing pulses and cardiac fat pad stimulation. Implantable cardiac devices include, for example, pacemakers, cardioverters, defibrillators, implantable cardioverter defibrillators, and the like. The term 'implantable cardiac device' or simply 'ICD' is used herein to refer to any implantable cardiac device. FIG. 1A and FIG. 2 illustrate such an environment in which embodiments of the present invention can be used.

Referring first to FIG. 1A, an exemplary ICD 10 is shown in electrical communication with a patient's heart 12 by way of three leads, 20, 24 and 30, suitable for delivering multi-chamber stimulation and pacing therapy. In addition, other subcutaneous (subQ) leads connecting with subQ electrodes can be used with the present invention (not shown). The subQ extra cardiac electrodes are preferably extra vascular and can be, e.g., paddle electrodes or coil electrodes mounted subcutaneously outside of the rib cage, but are not limited thereto. To sense atrial cardiac signals and to provide right atrial chamber stimulation therapy, the ICD 10 is coupled to the implantable right atrial lead 20 having at least an atrial tip electrode 22, which typically is implanted in the patient's right atrial appendage.

To sense left atrial and ventricular cardiac signals and to provide left-chamber pacing therapy, the ICD 10 is coupled to the 'coronary sinus' lead 24 designed for placement in the 'coronary sinus region' via the coronary sinus for positioning a distal electrode adjacent to the left ventricle and/or additional electrode(s) adjacent to the left atrium. As used herein, the phrase 'coronary sinus region' refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The ICD 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that RV coil electrode 36 will be positioned in the right ventricle and the SVC coil electrode 38 will be positioned in the SVC. Accordingly, the right ventricular lead 30 is capable of receiving cardiac signals and delivering stimulation in the form of pacing and shock therapy to the right ventricle.

FIG. 2 shows a simplified block diagram of the ICD 10, which is capable of treating SVT with pacing and stimulation of cardiac fat pads. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardiac fat pad stimulation and pacing.

A housing 240 of the ICD 10, shown schematically in FIG. 2, is often referred to as the 'can,' 'case' or 'case electrode' and may be programmably selected to act as the return electrode for all 'unipolar' modes. The housing 240 may further be used as a return electrode alone or in combination with one or more of the coil electrodes, 28, 36, and 38 for shocking purposes. The housing 240 further includes a connector (not shown) having a plurality of terminals, 242, 244, 246, 248, 252, 254, 256, 258, 264, 265, 266 and 267 (shown schematically and, for convenience, the names of the electrodes to which they are connected are shown next to many of the terminals). As such, to achieve right atrial sensing and pacing, the connector includes at least a right atrial tip terminal ($A_R$ TIP) 242 adapted for connection to the atrial tip electrode 22. Exemplary terminals 264, 265, 266 and 267 are for connecting to cardiac fat pad electrodes. More or less terminals can be included, as desired.

To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. To sense left atrial and ventricular cardiac signals and to provide left-chamber pacing therapy, the stimulation device 10 is coupled to a 'coronary sinus' lead 24 designed for placement in the 'coronary sinus region' via the coronary sinus for positioning a distal electrode adjacent to the left ventricle and/or additional electrode(s) adjacent to the left atrium. As used herein, the phrase 'coronary sinus region' refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

To achieve left chamber sensing, pacing and shocking, the connector includes at least a left ventricular tip terminal ($V_L$ TIP) 244, a left atrial ring terminal ($A_L$ RING) 246, and a left atrial shocking terminal ($A_L$ COIL) 248, which are adapted for connection via an exemplary coronary sinus lead 24, designed to receive left atrial and ventricular cardiac signals and to deliver left atrial and ventricular pacing therapy using at least a left ventricular tip electrode 26, left atrial pacing therapy using at least a left atrial ring electrode 27, and shocking therapy using at least a left atrial coil electrode 28.

To support right chamber sensing, pacing, and shocking the connector also includes a right ventricular tip terminal ($V_R$ TIP) 252, a right ventricular ring terminal ($V_R$ RING) 254, a right ventricular shocking terminal (RV COIL) 256, and an SVC shocking terminal (SVC COIL) 258, which are configured for connection to the right ventricular tip electrode 32, the right ventricular ring electrode 34, the RV coil electrode 36, and the SVC coil electrode 38, respectively.

The stimulation device 10 is also shown in electrical communication with the patient's heart 112 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 112 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals and delivering stimulation in the form of pacing and shock therapy to the right ventricle.

At the core of the ICD 10 is a programmable microcontroller 260, which controls the various modes of stimulation therapy. As is well known in the art, the microcontroller 260 typically includes one or more microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 260 includes the ability to process or monitor input signals (data) as controlled by a program code stored in a designated block of memory. The details of the design of the microcontroller 260 are not critical to the present invention. Rather, any suitable microcontroller 260 can be used to carry out the functions described herein. The use of microprocessor-based control circuits for performing timing and data analysis functions are well known in the art.

Representative types of control circuitry that may be used with the invention include the microprocessor-based control system of U.S. Pat. No. 4,940,052 to Mann et. al. which is expressly incorporated herein by reference in its entirety and the state-machines of U.S. Pat. Nos. 4,712,555 to Sholder which is expressly incorporated herein by reference in its entirety and 4,944,298 to Sholder which is expressly incorporated herein by reference in its entirety. For a more detailed description of the various timing intervals used within the ICD's and their inter-relationship, see U.S. Pat. No. 4,788,980 (Mann et. al.), which is expressly incorporated herein by reference in its entirety.

As shown in FIG. 2, an atrial pulse generator 270 and a ventricular pulse generator 272, generate pacing stimulation pulses for delivery by the right atrial lead 20, the right ventricular lead 30, and/or the coronary sinus lead 24 via an electrode configuration switch 274. More specifically, the atrial pulse generator 270 produces atrial pacing pulses (also known as A-pulses), and the ventricular pulse generator 272 produces ventricular pacing pulses (also known as V-pulses). In addition, a fat pad pulse generator 263 generates pulses to stimulate the cardiac fat pads. In order to provide stimulation therapy in each of the four chambers of the heart and to cardiac fat pads, the atrial, ventricular and fat pad pulse generators 270, 272 and 263 may include dedicated, independent pulse generators, multiplexed pulse generators, or shared pulse generators. The pulse generators 270, 272 and 263 are controlled by the microcontroller 260 via appropriate control signals 276, 278 and 262, respectively, to trigger or inhibit the stimulation pulses.

The microcontroller 260 further includes timing control circuitry 279, which is used to control pacing parameters (e.g., the timing of stimulation pulses) as well as to keep track of the timing of post ventricular atrial refractory period (PVARP) intervals, noise detection windows, evoked response windows, alert intervals, marker channel timing, etc., which are well known in the art. Examples of pacing parameters include, but are not limited to, atria-ventricular (AV) delay, inter-ventricular (RV-LV) delay, atrial inter-conduction (A-A) delay, ventricular inter-conduction (V-V) delay, and pacing rate.

The switch 274 includes a plurality of switches for connecting the desired electrodes to the appropriate I/O circuits, thereby providing complete electrode programmability. Accordingly, the switch 274, in response to a control signal 280 from the microcontroller 260, determines the polarity of the stimulation pulses (e.g., unipolar, bipolar, combipolar, etc.) by selectively closing the appropriate combination of switches (not shown) as is known in the art.

The atrial sensing circuits 282 and ventricular sensing circuits 284 may also be selectively coupled to the right atrial lead 20, the coronary sinus lead 24, and the right ventricular lead 30, through the switch 274 for detecting the presence of cardiac activity in each of the four chambers of the heart. Accordingly, the atrial (ATR. SENSE) and ventricular (VTR. SENSE) sensing circuits 282 and 284 may include dedicated sense amplifiers, multiplexed amplifiers, or shared amplifiers. The switch 274 determines the 'sensing polarity' of the cardiac signal by selectively closing the appropriate switches, as is also known in the art. In this way, a clinician may program the sensing polarity independent of the stimulation polarity.

Each of the sensing circuits, 282 and 284 preferably employs one or more low power, precision amplifiers with programmable gain and/or automatic gain control, band pass filtering, and a threshold detection circuit, as known in the art, to selectively sense the cardiac signal of interest. For example, the atrial sensing circuit 282 can sense P-waves and the ventricular sensing circuit 284 can sense R-waves. A P-wave occurs when that atrium contracts naturally, and is thus indicative of an intrinsic atrial contraction. Similarly, an R-wave occurs when the ventricle contracts naturally, and is thus indicative of an intrinsic ventricular contraction. As explained in U.S. Pat. No. 6,865,420, to Kroll, which is expressly incorporated herein by reference in its entirety, it is also possible that the ICD 10 includes further sensing circuitry (not shown) that is dedicated to sensing a cardiac signal that is evaluated for changes indicative of myocardial ischemia by an ischemia detector (not shown).

It is well known in the art to detect P-waves and R-waves using thresholding, where corresponding thresholds (e.g., a P-wave threshold and an R-wave threshold) can be either constant or dynamically adjustable. Examples of dynamically adjustable thresholds are provided, for example, in U.S. Pat. No. 4,768,511 to DeCote, and U.S. Pat. No. 5,891,048 to Nigam et al and in commonly assigned U.S. patent application Ser. No. 10/948,026 to Nabutovsky et al., filed Nov. 24, 2004, each of which is expressly incorporated by reference herein in their entirety. Using thresholding algorithms, and/or alternative types of algorithms, it also is well known how to detect the approximate locations of P-waves and R-waves.

The outputs of the atrial and ventricular sensing circuits 282 and 284 are connected to the microcontroller 260 which, in turn, are able to trigger or inhibit the atrial and ventricular pulse generators 270 and 272, respectively, in a demand fashion in response to the absence or presence of cardiac activity, in the appropriate chambers of the heart. The atrial pulse generator 270 provides an A-pulse for delivery to the atrium at appropriate times, e.g., on demand as needed to maintain a programmed or sensor-indicated heart rate. The ventricular pulse generator 272 similarly provides a V-pulse for delivery to the ventricle at appropriate times, e.g., on demand as needed to maintain a programmed or sensor-indicated heart rate. The fat pad pulse generator 263 provides stimulation to cardiac fat pads, in response to a control signals received over control signal line 262 from the microcontroller 260. The sensing circuits 282 and 284 receive control signals over signal lines 286 and 288 from the microcontroller 260 for purposes of sensing and controlling the gain, threshold, polarization charge removal circuitry (not shown), and timing of any blocking circuitry (not shown) coupled to the inputs of the sensing circuits 282 and 284.

For arrhythmia detection, the ICD 10 utilizes the atrial and ventricular sensing circuits 282 and 284 to sense cardiac signals to determine whether a rhythm is physiologic or pathologic. The timing intervals between sensed events (e.g., P-waves, R-waves, and depolarization signals associated with fibrillation are then classified by microcontroller 260 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardio version shocks or defibrillation shocks, collectively referred to as 'tiered therapy').

The microcontroller 260 can also utilize an arrhythmia detector 275 and a morphology detector 277 to recognize and classify arrhythmias so that appropriate therapy can be delivered. The morphology detector 277 may also be used to detect signal morphologies that are useful for detecting or confirming ischemic events. The arrhythmia detector 275 and morphology detector 277 can be implemented within the microcontroller 260, as shown in FIG. 2. Thus, these elements can be implemented by software, firmware, or combinations thereof. It is also possible that all, or portions, of these detectors can be implemented using hardware. In accordance with embodiments of the present invention the arrhythmia detector 275 can monitor for and detect SVT. Alternatively, a separate SVT detector 261 can be provided, if desired.

Cardiac signals are also applied to the inputs of an analog-to-digital (A/D) data acquisition system 290. The data acquisition system 290 is configured to acquire intra-cardiac electrogram (EGM) signals, convert the raw analog data into a digital signal (e.g., consisting of samples), and store the digital signals for later processing and/or telemetric transmission to an external device 202. Data acquisition system 290 is coupled to the right atrial lead 20, the coronary sinus lead 24, and right ventricular lead 30 through switch 274 to sample cardiac signals across any pair of desired electrodes.

Figure 1B:
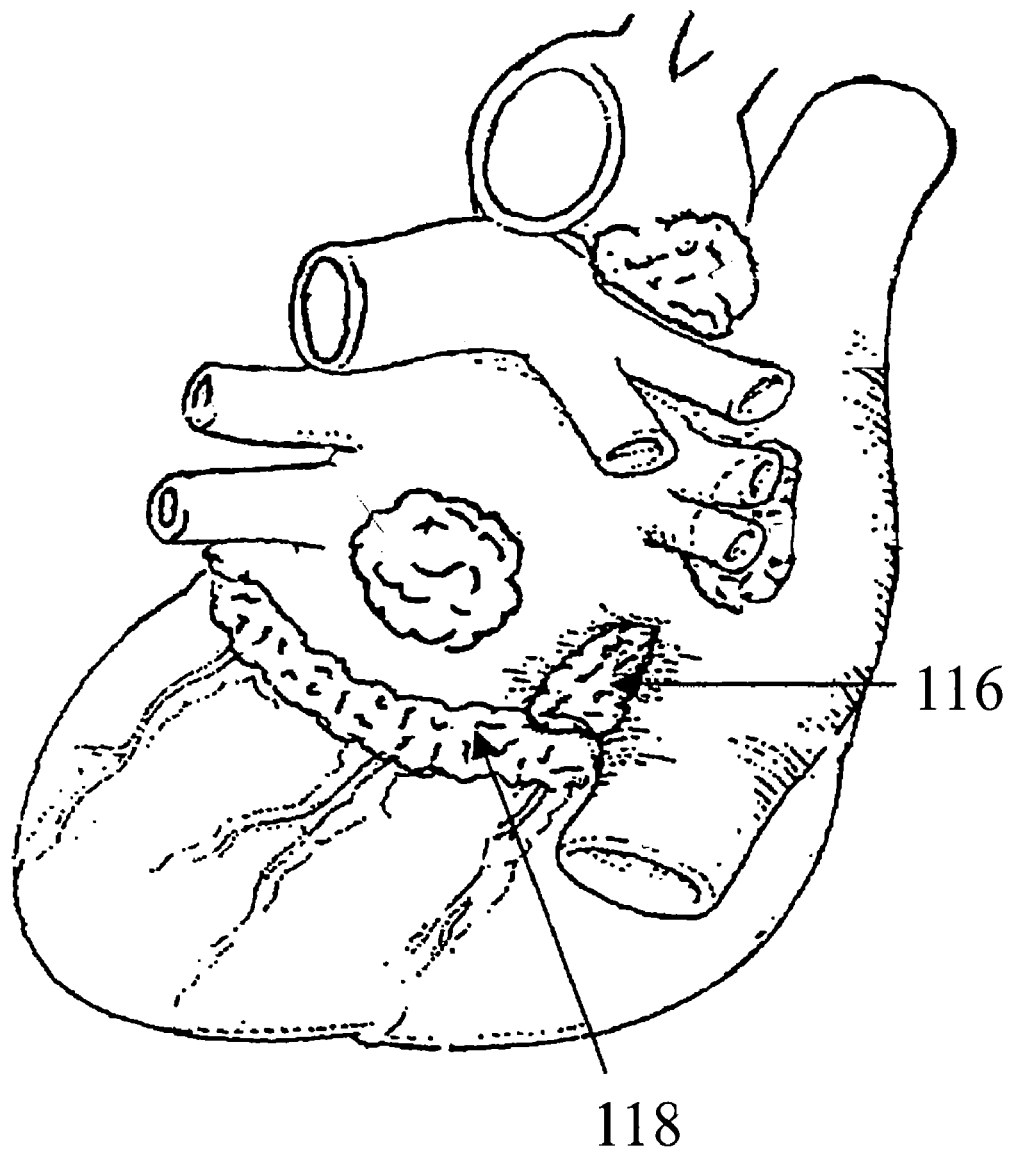
FIG. 1B shows two fat pad regions on or near the heart.

Cardiac fat pat stimulation can be accomplished, e.g., either directly by electrode placement on/or around one or more cardiac fad pad (e.g., by placing the electrode in contact with ganglionated plexi (GP) or indirectly via electrode placement in the vicinity of the GP). For example, FIG. 1B shows the two sites 116 and 118 for cardiac fat pad electrodes capable of delivering stimulation to a patient's GP. Such electrodes can be optimally positioned, e.g., in the epicardial fat pad near inferior vena cava-left atrial (IVC-ILA) fat pad 116 or the coronary sinus (CS) fat pad 118. Other possible locations for the stimulation electrodes are in proximity to the cervical vagus where they are also capable of delivering stimulation bursts to the patient's vagus nerve to achieve the same effect. Additional and/or alternative locations for the cardiac fat pad stimulation electrodes are within the scope of the present invention, some of which are discussed below. Preferably, the stimulation electrode(s) are located such that they can deliver stimulation to a cardiac fat pad or the vagal branches that innervate the cardiac fat pads. Preferably, such cardiac fat pad(s) innervate the AV node and/or ventricular tissue.

The ICD 10 further includes a physiologic sensor 208 that can be used to detect changes in cardiac performance or changes in the physiological condition of the heart. Accordingly, the microcontroller 260 can respond by adjusting the various pacing parameters (such as rate, AV Delay, RV-LV Delay, V-V Delay, etc.). The microcontroller 260 controls adjustments of pacing parameters by, for example, controlling the stimulation pulses generated by the atrial and ventricular pulse generators 270 and 272. While shown as being included within the ICD 10, it is to be understood that the physiologic sensor 208 may also be external to the ICD 10, yet still be implanted within or carried by the patient. More specifically, the sensor 208 can be located inside the ICD 10, on the surface of ICD 10, in a header of ICD 10, or on a lead (which can be placed inside or outside the bloodstream).

Also shown in FIG. 2 is an activity sensor 217. The activity sensor 217 (e.g., an accelerometer) can be used to determine the activity of the patient. Such information can be used for rate responsive pacing, or to determine whether the patient is sufficiently at rest such that certain baseline measurements can be obtained. If the sensor 217 is a multi-dimensional accelerometer, then posture information can also be extracted. The following patents, which are expressly incorporated herein by reference in their entirety, describe exemplary activity sensors that can be used to detect activity of a patient (some also detect posture): U.S. Pat. No. 6,658,292 to Kroll et al., entitled "Detection of Patient's Position and Activity Status using 3D Accelerometer-Based Position Sensor"; U.S. Pat. No. 6,466,821 to Kroll et al., entitled "Orientation of Patient's Position Sensor using External Field"; and U.S. Pat. No. 6,625,493 to Pianca et al., entitled "AC/DC Multi-Axis Accelerometer for Determining Patient Activity and Body Position". Simple activity sensors employ a piezoelectric crystal or a cantilever beam having a film of a piezoelectric polymer adhered to a surface of the beam. These are just a few exemplary types of activity sensors 217, which are not meant to be limiting.

The ICD 10 may also include a magnet detection circuitry (not shown), coupled to the microcontroller 260. It is the purpose of the magnet detection circuitry to detect when a magnet is placed over the ICD 10. A clinician may use the magnet to perform various test functions of the ICD 10 and/or to signal the microcontroller 260 that the external programmer 202 is in place to receive or transmit data to the microcontroller 260 through the telemetry circuit 201.

As further shown in FIG. 2, the ICD 10 can have an impedance measuring circuit 213, which is enabled by the microcontroller 260 via a control signal 214. The known uses for an impedance measuring circuit 213 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 213 is advantageously coupled to the switch 274 so that any desired electrode may be used. The impedance measuring circuit 213 is not critical to the present invention and is shown only for completeness.

In the case where the ICD 10 is intended to operate as a cardioverter, pacer or defibrillator, it should detect the occurrence of an arrhythmia and automatically apply an appropriate electrical therapy to the heart aimed at terminating the detected arrhythmia. To this end, microcontroller 260 further controls a shocking circuit 216 by way of a control signal 218. The shocking circuit 216 generates shocking pulses of low (up to about 0.5 Joules), moderate (about 0.5-10 Joules), or high energy (about 11 to 40 Joules), as controlled by the microcontroller 260. Such shocking pulses are applied to the patient's heart 12 through at least two shocking electrodes (e.g., selected from the left atrial coil electrode 28, the RV coil electrode 36, and the SVC coil electrode 38). As noted above, the housing 240 may act as an active electrode in combination with the RV electrode 36, or as part of a split electrical vector using the SVC coil electrode 38 or the left atrial coil electrode 28 (i.e., using the RV electrode as a common electrode).

Cardio-version shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of about 5-40 Joules), delivered asynchronously (since R-waves may be too disorganized to be recognize), and pertaining exclusively to the treatment of fibrillation. Accordingly, the microcontroller 260 is capable of controlling the synchronous or asynchronous delivery of the shocking pulses.

Advantageously, a data acquisition system 290 can be coupled to the microcontroller 260, or other detection circuitry, for detecting an evoked response from the heart 12 in response to an applied stimulus, thereby aiding in the detection of 'capture'. Capture occurs when an electrical stimulus applied to the heart is of sufficient energy to depolarize the cardiac tissue, thereby causing the heart muscle to contract. The microcontroller 260 detects a depolarization signal during a window following a stimulation pulse, the presence of which indicates that capture has occurred. The microcontroller 260 enables capture detection by triggering the ventricular pulse generator 272 to generate a stimulation pulse, starting a capture detection window using the timing control circuitry 279 within the microcontroller 260, and enabling the data acquisition system 290 via control signal 292 to sample the cardiac signal that falls in the capture detection window and, based on the amplitude, determines if capture has occurred.

The implementation of capture detection circuitry and algorithms are well known. See for example, U.S. Pat. No. 4,729,376 to Decote, Jr. which is expressly incorporated herein by reference in its entirety; U.S. Pat. No. 4,708,142 to Decote, Jr. which is expressly incorporated herein by reference in its entirety; U.S. Pat. No. 4,686,988 to Sholder which is expressly incorporated herein by reference in its entirety; U.S. Pat. No. 4,969,467 to Callaghan et. al. which is expressly incorporated herein by reference in its entirety; and U.S. Pat. No. 5,350,410 to Mann et. al. which is expressly incorporated herein by reference in its entirety. The type of capture detection system used is not critical to the present invention.

The microcontroller 260 is further coupled to a memory 294 by a suitable data/address bus 296, wherein the programmable operating parameters used by the microcontroller 260 are stored and modified, as required, in order to customize the operation of the device 10 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart 12 within each respective tier of therapy.

Advantageously, the operating parameters of the implantable device 10 can be non-invasively programmed into the memory 294 through a telemetry circuit 201 in telemetric communication with the external device 202, such as a programmer, trans telephonic transceiver, or a diagnostic system analyzer. The telemetry circuit 201 can be activated by the microcontroller 260 by a control signal 206. The telemetry circuit 201 advantageously allows intra cardiac electrograms and status information relating to the operation of the device 10 (as contained in the microcontroller 260 or memory 294) to be sent to an external device 202 through an established communication link 205.

For examples of such devices, see U.S. Pat. No. 4,809,697, to Causey, III et al. entitled "Interactive Programming and Diagnostic System for use with Implantable Pacemaker" which is expressly incorporated herein by reference in its entirety; U.S. Pat. No. 4,944,299, to Silvian entitled "High Speed Digital Telemetry System for Implantable Device" which is expressly incorporated herein by reference in its entirety; and U.S. patent application Ser. No. 09/223,422, to McClure et al. filed Dec. 30, 1998, entitled "Efficient Generation of Sensing Signals in an Implantable Medical Device such as a Pacemaker or ICD" which is expressly incorporated herein by reference in its entirety.

The pacing device 10 additionally includes a battery 211, which provides operating power to all of the circuits shown in FIG. 2. If the pacing device 10 also employs shocking therapy, the battery 211 can be capable of operating at low current drains for long periods of time, and then be capable of providing high-current pulses (for capacitor charging) when the patient requires a shock pulse. The battery 211 can also have a predictable discharge characteristic so that elective replacement time can be detected.

Figure 3:
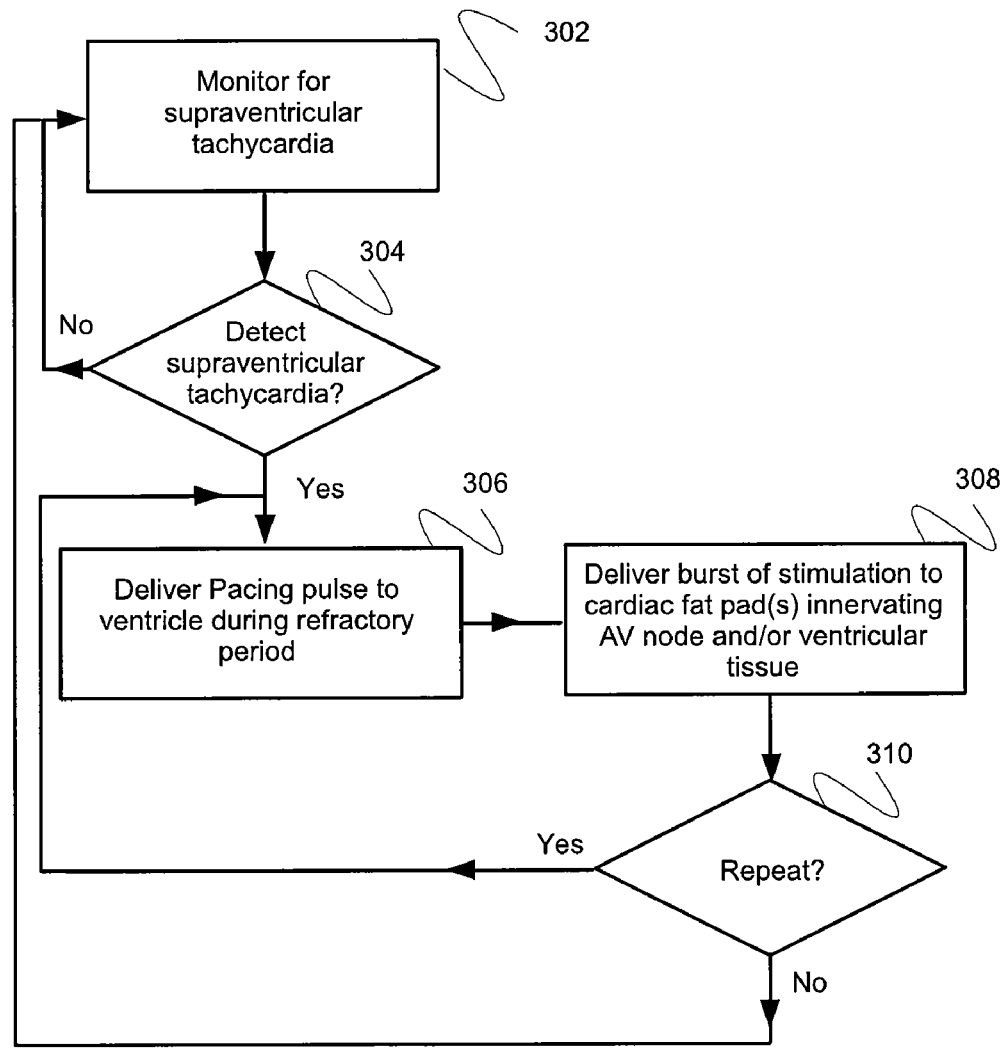
FIG. 3 is a high level flow diagram useful for describing methods for reducing a ventricular rate during a SVT, and preferably terminating the SVT, in according with embodiments of the present invention.

Now that an exemplary implantable stimulation device has been described, specific embodiments of the present invention will be now be described with reference to the high level flow diagram of FIG. 3 and the timing diagrams of FIGS. 4A and 4B. In FIG. 3, the flow diagram provides an overview of the operation and novel features that can be implemented in various embodiments of the device 10. In the flow diagram, the various algorithmic steps are summarized in individual 'blocks'. Such blocks describe specific actions or decisions that are made or carried out as the algorithm proceeds. Where a microcontroller (or equivalent) is employed, the flow diagram presented herein provides the basis for a 'control program' that may be used by such a microcontroller (or equivalent) to effectuate the desired control of the stimulation device. Those skilled in the art may readily write such a control program based on the flow diagram and other descriptions presented herein.

More specifically, FIG. 3 is a high level flow diagram useful for describing methods for reducing a ventricular rate during a SVT, and preferably terminating the SVT, in according with embodiments of the present invention. Referring to FIG. 3, at a step 302 an EGM is monitored for the purpose of detecting a SVT, such as AF. At a step 304, there is a determination of weather a SVT has been detected. Exemplary electrodes useful for monitoring for SVT were discussed above with reference to FIG. 1 and FIG. 2. As mentioned above, the arrhythmia detector 275 or the dedicated SVT detector 261 can be used to perform steps 302 and 304. Since it is well known how to monitor for and detect a SVT, there is no need to describe steps 302 and 304 in additional detail.

In response to SVT being detected at step 304, a ventricular pacing pulse is delivered during a refractory period following a ventricular activation at step 306, to thereby extend the refractory period, and slow the ventricular rate. For example, the left ventricular tip electrode 26 the right ventricular tip electrode 32 and/or the right ventricular ring electrode 36 can be used to deliver a ventricular pacing pulse. The ventricular activation is most likely an intrinsic ventricular activation, which is detectable as an R-wave of the EGM.

Still referring to FIG. 3, in addition to delivering a ventricular pacing pulse, a burst of stimulation is delivered to one or more cardiac fat pad at step 308, to slow atrioventricular (AV) conduction. The cardiac fat pad stimulation burst can be delivered, e.g., using electrode(s) placed at locations 116 and/or 118, which were discussed above with reference to FIG. 1B. Stimulatory fat pad electrodes 266 and 267 (see FIG. 2) placed at fat pad positions 116 and 118 (see FIG. 1B) can be used for providing stimulation at the fat pad positions. Preferably at least one cardiac fat pad to which stimulation is delivered innervates atrioventricular (AV) node tissue and/or ventricular tissue. This is because the desire is to control the AV node and/or ventricles. In contrast, if a cardiac fat pad that innervates an atrium were to be stimulated, that would likely further increase the atrial rate, which is undesirable.

In accordance with specific embodiments, the burst of stimulation can be delivered to one or more cardiac fat pad continuously for between approximately 100 msec and approximately 1 sec. The frequency of the pulsed cardiac fat pad stimulation burst waveform can be between approximately 15 Hz and approximately 50 Hz. The amplitude of the burst of stimulation pulses can be between approximately 0.1 volts and approximately 10 volts, and the pulse width between approximately 1 msec and approximately 3 msec. It is expected that at the above cardiac fat pad stimulation levels, an additional ~15% drop in heart rate can be achieved. As explained above, it is desired that the bursts of stimulation not cause pain to the patient. The level at which a patient feels pain differs from patient to patient. Accordingly, stimulation bursts at various different amplitudes can be delivered to the patient of interest, e.g., during implantation, to determine at what amplitude the patient will feel pain. Then the cardiac device can be programmed to deliver bursts of stimulation having an amplitude that is less than the amplitude at which the patient will feel pain.

In specific embodiments, steps 306 and 308 can be repeated a plurality of times in response to a SVT being detected, as indicated at step 310. For example, steps 306 and 308 can be performed a predetermined amount of times (e.g., for each of a plurality of consecutive R waves), until a ventricular rate is within an acceptable rate, or until a SVT has otherwise been terminated. This will be better understood from the timing diagrams discussed below, with reference to FIGS. 4A and 4B.

Additional details of the ventricular pacing pulse delivered at step 306 and the burst of cardiac fat pad stimulation delivered at step 308 will now be described with reference to FIGS. 4A and 4B. As shown in FIG. 4A, at a time T1 (within a refractory period) after a sensed R wave, a ventricular pacing pulse is delivered. As mentioned above, this has the effect of extending the refractory period. After a further delay, t, the cardiac fat pad stimulation occurs for a time duration of T2. In this embodiment, the cardiac fat pad stimulation is terminated a period of time prior to detection of the next R wave, as indicated by the delta (☐.

As mentioned above, the scheme described can be repeated multiple times. For example, the scheme can be repeated a predetermined plurality of times, or until the ventricular rate is slowed to at least a specified level. More specifically, a ventricular pacing pulse followed by a burst of cardiac fat pad stimulation can be delivered following each of a plurality of sensed R waves. While it is preferably that the ventricular pacing pulse followed by the burst of cardiac fat pad stimulation occurs following each of a plurality of consecutive sensed R waves, it is also possible that some R waves be skipped, e.g., that this occurs only following every other sensed R wave, or the like. The time period T1, delay t and duration T2 can be the same each time the scheme is repeated, or these variables can be changed (e.g., slowly increased or slowly decreased), depending on how the algorithm is programmed.

In accordance with specific embodiments, sensing amplifiers (e.g., 282 and 284) of a device are blanked during delivery of cardiac fat pad stimulation to avoid over sensing. Then, after the end of a stimulation burst, sensing channels are re-enabled to detect a first intrinsic activation conducted through an AV node that captures the ventricles.

In accordance with specific embodiments, the delay time 't' between the ventricle stimulation and delivery of the stimulation burst is specified to achieve optimal ventricular rate slowing. Further, the burst voltage, frequency, and pulse width can be optimized to give a maximum negative dromotropic effect during the short interval T2 without causing pain to the patient.

Further embodiments of the present invention will now be explained with reference to the timing diagram of FIG. 4B. In these embodiments, an initial period of cardiac fat pad stimulation is introduced during the T1 time interval discussed above with reference to FIG. 4A, and thus, prior to the ventricular pacing pulse. In the embodiment of FIG. 4B, the duration of the initial cardiac fat pad stimulation prior to the ventricular pacing pulse (i.e., during T1) can be the same as or different than the duration of the cardiac fat pad stimulation delivered during time period T2. Also, there can be a delay after the R wave is detected, before the initial cardiac fat pad stimulation is delivered. Similarly, there can be a delta after the initial cardiac fat pad stimulation delivery ends before the ventricular pacing pulse is delivered. Following the delivery of the ventricular pacing pulse, there is a delay, t, after which the cardiac fat pad stimulation is delivered for the time period T2. The cardiac fat pad stimulation is terminated a delta ☐ before the next R wave is detected.

Figure 4A:
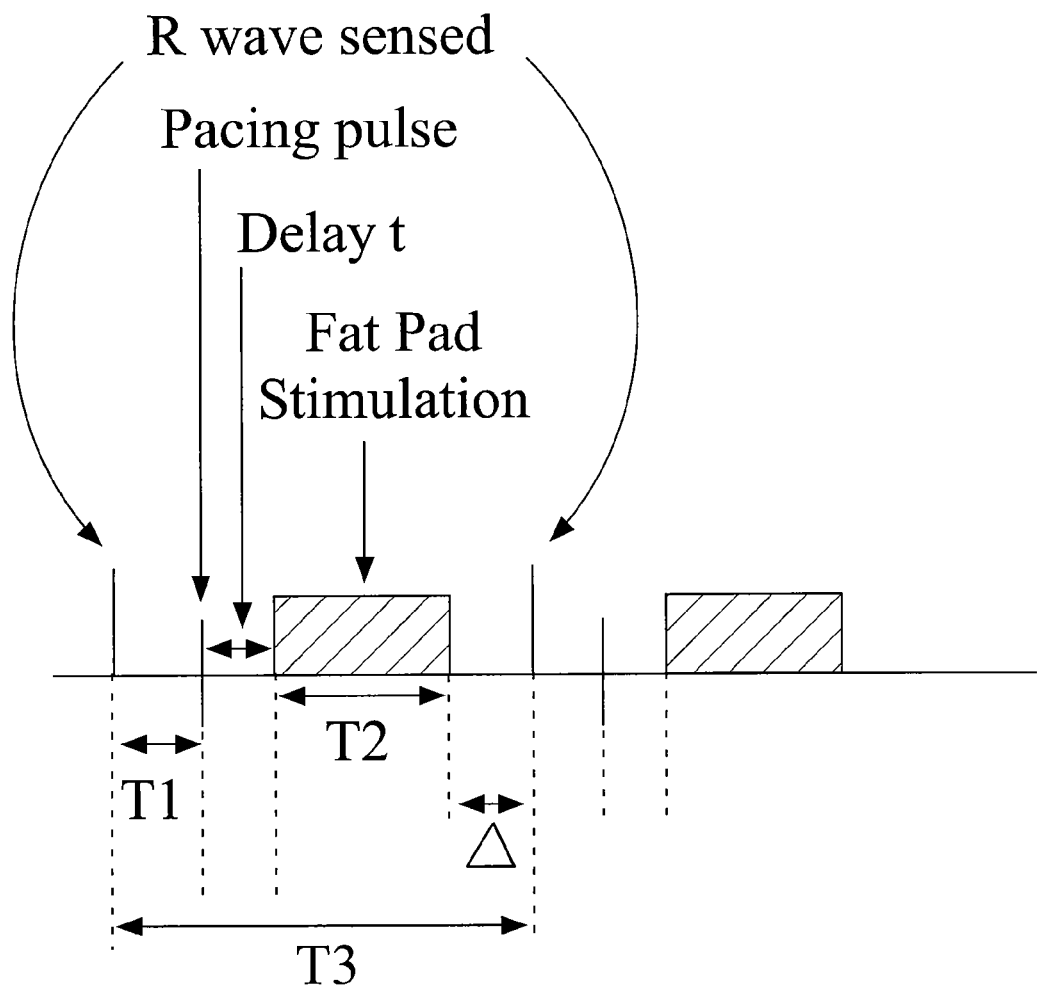
FIG. 4A is a high level timing diagram useful for showing a ventricular pacing and cardiac fat pad stimulation scheme as per an embodiment of the present invention.
Figure 4B:
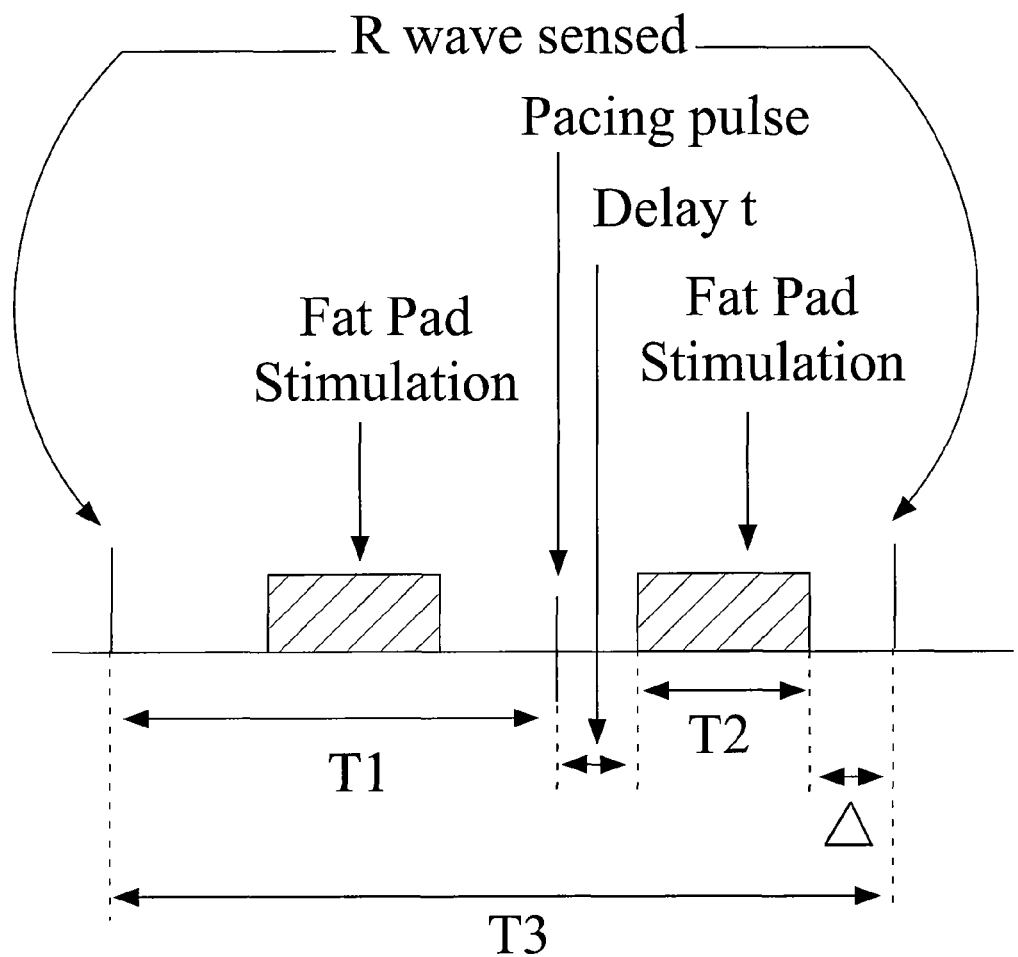
FIG. 4B is a high level timing diagram useful for showing a ventricular pacing and cardiac fat pad stimulation scheme as per an alternative embodiment of the present invention.

In the schemes shown in FIGS. 4A and 4B, the desired time between sensed R-waves (i.e., T3) can be a programmable value that is predefined by a user or set by a device depending on a detected V-rate during an arrhythmia.

In various embodiments of the present invention, a variety of other combinations of cardiac fat pad stimulation bursts and pacing can be used. In another embodiment of the present invention, delivery of a ventricular pace pulse and cardiac fat pad stimulation can be commenced simultaneously. In this manner low amplitude high frequency stimulation performed in conjunction with ventricular pacing during the refractory period can be used to produce an optimal ventricular rate during SVT (e.g., AF).

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein.

Thus, the breadth and scope of the present invention should not be limited by any of the above-described exemplary embodiments, but should be defined only in accordance with the following claims and their equivalents.

What is claimed is:

1. For use with an implantable system, a method for painlessly reducing a patient's ventricular rate during a supra ventricular tachycardia (SVT), comprising:
   (a) programming a cardiac fat pad stimulation amplitude that is lower than a level at which the patient will feel pain;
   (b) monitoring for a SVT; and
   (c) painlessly reducing the ventricular rate in response to detecting a SVT by,
   (c.1) delivering a pacing pulse to a ventricle during a refractory period following an intrinsic ventricular activation, to thereby extend the refractory period; and
   (c.2) prior to the next intrinsic ventricular activation, delivering a burst of stimulation to one or more cardiac fat pad that innervates at least one of atrioventricular (AV) node tissue and ventricular tissue, to slow AV node conduction, wherein an amplitude of the burst of stimulation is the programmed cardiac fat pad stimulation amplitude that is lower than the level at which the patient will feel pain.

2. The method of claim 1, where in step (c.1) the pacing pulse is delivered to a ventricle prior to ventricular repolarization.

3. The method of claim 1, where in step (c.2) the burst of stimulation is delivered to a cardiac fat pad that innervates AV node tissue.

4. The method of claim 1, where in step (c.2) the burst of stimulation is delivered to a cardiac fat pad that innervates ventricular tissue.

5. The method of claim 1, where in step (c.1) the pacing pulse is delivered T1 seconds after the intrinsic ventricular activation is detected, wherein T1 is between:
   a lower limit of approximately 10 msec; and
   an upper limit of approximately 100 msec.

6. The method of claim 1, wherein the burst of stimulation delivered at step (c.2) follows the pacing pulse delivered in step (c.1) by between:
   a lower limit of approximately 10 msec; and
   an upper limit of approximately 30 msec.

7. The method of claim 1, where in step (c.2) duration of the burst of stimulation is T2 seconds, wherein T2 is between:
   a lower limit of approximately 100 msec; and
   an upper limit of approximately 1 sec.

8. The method of claim 1, where in step (c.2) a frequency of the burst of stimulation is between:
   a lower limit of approximately 15 Hz; and
   an upper limit of approximately 50 Hz.

9. The method of claim 1, where in step (c.2) pulses of the burst of stimulation have a pulse width between:
   a lower limit of approximately 0.5 msec; and
   an upper limit of approximately 3 msec.

10. The method of claim 1, where in step (c.2 the amplitude of the burst of stimulation, which is the programmed cardiac fat pad stimulation amplitude that is lower than the level at which the patient will feel pain, is between:
    a lower limit of approximately 1 volt; and
    an upper limit of approximately 10 volts.

11. The method of claim 10, wherein step (a) comprises:
    determining at what amplitude the patient feels pain in response to the type of stimulation to be delivered at step (c.2); and
    programming the cardiac fat pad stimulation amplitude to be lower than the amplitude at which it was determined that the patient feels pain in response to the type of stimulation to be delivered at step (c.2).

12. The method of claim 1, wherein commencement of the burst of stimulation delivered at step (c.2) coincides approximately in time with the pacing pulse delivered at step (c.1).

13. The method of claim 1, further comprising, prior to delivering a pacing pulse to a ventricle at step (c.1), delivering an initial burst of stimulation to one or more cardiac fat pad that innervates at least one of atrioventricular (AV) node tissue and ventricular tissue.

14. The method of claim 1, wherein in response to detecting a SVT steps (c.1) and (c.2) are performed for each of a plurality of consecutive ventricular activations.

15. The method of claim 1, wherein in response to detecting a SVT steps (c.1) and (c.2) are repeated for each of a plurality of consecutive ventricular activations, until a desired ventricular rate is obtained.

16. In response to detecting a supra ventricular tachycardia (SVT) in a patient, a method for painless treatment of the SVT comprising:
    delivering the following between consecutive sensed intrinsic ventricular activations
    a pacing pulse to a ventricle during a refractory period; and
    a burst of stimulation to one or more cardiac fat pad that innervates at least one of atrioventricular (AV) node tissue and ventricular tissue, wherein an amplitude of the burst of stimulation is a programmed cardiac fat pad stimulation amplitude that is lower than a level at which the patient will feel pain.

17. The method of claim 16, where a frequency of the burst of stimulation is between:
    a lower limit of approximately 15 Hz; and
    an upper limit of approximately 50 Hz.

18. The method of claim 16, where the pulse width of the burst of stimulation is between:
    a lower limit of approximately 0.5 msec; and
    an upper limit of approximately 3 msec.

19. The method of claim 16, where the amplitude of the burst of stimulation, which is the programmed cardiac fat pad stimulation amplitude that is lower than the level at which the patient will feel pain, is between:
    a lower limit of approximately 1 volt; and
    an upper limit of approximately 10 volts.

20. The method of claim 19, further comprising:
    determining at what amplitude a patient feels pain in response to the stimulation to be delivered to the one or more cardiac fat pad to treat a SVT;
    programming the cardiac fat pad stimulation amplitude to be lower than the amplitude at which it was determined that the patient feels pain in response to the stimulation to be delivered to the one or more cardiac fat pad to treat a SVT; and when treating a SVT, the amplitude of the burst of stimulation delivered to the one or more cardiac fat pad is the programmed cardiac fat pad stimulation amplitude that is less than the amplitude at which the patient feels pain.

21. An implantable system adapted to painlessly reduce ventricular rate during a supra ventricular tachycardia (SVT), comprising:

memory to store a cardiac fat pad stimulation amplitude that is lower than a level at which the patient will feel pain;

a monitor to monitor for SVT;

one or more pulse generator;

at least one pacing electrode to deliver pacing pulses to a ventricle; and at least one stimulation electrode to deliver stimulation to one or more cardiac fat pad that innervates at least one of atrio-ventricular (AV) node tissue and ventricular tissue;

where, in response to the monitor detecting a SVT, the one or more pulse generator generates and delivers, via at least one said pacing electrode, a pacing pulse to a ventricle during a refractory period following an intrinsic ventricular activation, to thereby extend the refractory period; and generates and delivers, via at least one said stimulation electrode, prior to the next intrinsic ventricular activation, a burst of stimulation to one or more cardiac fat pad that innervates at least one of AV node tissue and ventricular tissue, to slow AV node conduction, wherein an amplitude of the burst of stimulation is the programmed cardiac fat pad stimulation amplitude that is lower than the level at which the patient will feel pain.

* * * * *